United States Patent
Klimov et al.

(10) Patent No.: US 9,117,107 B2
(45) Date of Patent: Aug. 25, 2015

(54) DEVICE FOR BIOMETRICALLY CONTROLLING A FACE SURFACE

(75) Inventors: Andrey Vladimirovich Klimov, Moscow (RU); Sergey Vladimirovich Suhovey, Moscow (RU); Artem Leonidovich Yukhin, Moscow (RU)

(73) Assignee: Bioscrypt, Inc., Sunnyvale, CA (US)

( * ) Notice: Subject to any disclaimer, the term of this patent is extended or adjusted under 35 U.S.C. 154(b) by 2055 days.

(21) Appl. No.: 11/573,548

(22) PCT Filed: Apr. 20, 2005
(Under 37 CFR 1.47)

(86) PCT No.: PCT/RU2005/000210
§ 371 (c)(1),
(2), (4) Date: Apr. 21, 2008

(87) PCT Pub. No.: WO2006/031143
PCT Pub. Date: Mar. 23, 2006

(65) Prior Publication Data
US 2009/0021579 A1    Jan. 22, 2009

(30) Foreign Application Priority Data

Aug. 12, 2004    (RU) .............................. 2004-000312

(51) Int. Cl.
| | |
|---|---|
| *H04N 7/18* | (2006.01) |
| *G06K 9/00* | (2006.01) |
| *A61B 5/117* | (2006.01) |

(52) U.S. Cl.
CPC .......... *G06K 9/00221* (2013.01); *A61B 5/1176* (2013.01); *G06K 9/00255* (2013.01); *G06K 9/00912* (2013.01)

(58) Field of Classification Search
USPC ............................ 348/77, 79, 207.1; 382/181
See application file for complete search history.

(56) References Cited

U.S. PATENT DOCUMENTS

| | | | |
|---|---|---|---|
| 4,349,277 A | 9/1982 | Mundy et al. | |
| 4,460,921 A | 7/1984 | Henry et al. | |

(Continued)

FOREIGN PATENT DOCUMENTS

| | | |
|---|---|---|
| DE | 3718151 | 12/1987 |
| DE | 19749435 | 5/1999 |

(Continued)

OTHER PUBLICATIONS

Tajima, J., et al., "3-D data acquisition by Rainbow Range Finder," Pattern Recognition, 1990. Proceedings., 10th International Conference on Pattern Recognition, Jun. 16-21, 1990, pp. 309-313, vol. 1, No. 10.

(Continued)

*Primary Examiner* — Ranodhi Serrao
(74) *Attorney, Agent, or Firm* — Nixon & Peabody LLP

(57) ABSTRACT

A device for biometrically controlling a face surface includes a camera, a unit for displaying a face position, a computer and an illumination unit. The illumination unit includes a transparency and an objective lens for projecting the transparency image on the face, which is located in such a way that the optical axes of the objective of the illumination unit and of the camera are disposed on the same plane at an angle with respect to each other. The unit for displaying the face position is embodied and disposed in such a way that it makes it possible to display the symmetrical face position with respect to the plane formed by the optical axes of the objective lenses of the illumination unit and the camera.

20 Claims, 2 Drawing Sheets

(56) References Cited

U.S. PATENT DOCUMENTS

| | | | |
|---|---|---|---|
| 4,737,845 A | 4/1988 | Susuki et al. | |
| 5,461,417 A | 10/1995 | White et al. | |
| 5,615,003 A | 3/1997 | Hermary et al. | |
| 5,640,962 A | 6/1997 | Benedikt et al. | |
| 5,717,512 A | 2/1998 | Chmielewski et al. | |
| 5,890,787 A * | 4/1999 | McNelley et al. | 353/28 |
| 5,982,912 A * | 11/1999 | Fukui et al. | 382/118 |
| 6,056,404 A * | 5/2000 | Kawai et al. | 351/237 |
| 6,111,580 A * | 8/2000 | Kazama et al. | 715/863 |
| 6,323,761 B1 * | 11/2001 | Son | 340/426.35 |
| 6,377,700 B1 | 4/2002 | Mack et al. | |
| 6,388,639 B1 * | 5/2002 | Hoshino et al. | 345/8 |
| 6,927,854 B2 | 8/2005 | Hirabayashi et al. | |
| 2002/0006222 A1 | 1/2002 | Inagaki et al. | |
| 2003/0123713 A1 | 7/2003 | Geng | |
| 2004/0218788 A1 | 11/2004 | Geng | |
| 2005/0111705 A1 | 5/2005 | Waupotitsch et al. | |
| 2005/0225662 A1 | 10/2005 | Tsuda et al. | |

FOREIGN PATENT DOCUMENTS

| | | |
|---|---|---|
| EP | 0076866 A | 4/1983 |
| JP | 6044365 | 2/1996 |
| JP | 2003030684 | 1/2003 |
| RU | 2184933 | 7/2002 |
| RU | 2185598 | 7/2002 |
| RU | 2251748 | 9/2003 |
| WO | WO 00/70303 | 11/2000 |
| WO | 2006/031147 | 3/2006 |

OTHER PUBLICATIONS

Valente, Stephane, et al., "A visual analysis/synthesis feedback loop for accurate face tracking", Signal Processing: Image Communication, Elsevier Science Publishers, Amsterdam, NL., vol. 16, No. 6, Feb. 1, 2001, pp. 585-608.

Wust, C., et al., "Surface profile measurement using color fringe projection," Machine Vision and Applications, Jun. 1991, pp. 193-203, vol. 4, No. 3.

Koziol, Stephen R., USPTO Office Communication dated Apr. 29, 2009 in relation to U.S. Appl. No. 11/485,745, filed Jul. 12, 2006 (8 pages).

PCT International Search Report, PCT/RU2005/000210, Aug. 25, 2005, 1 page.

Supplementary European Search Report for Application No. EP 05735484.7, dated Apr. 17, 2012, 3 pages.

Kotov, A., International Search Report, International Application No. PCT/RU2005/000210, Aug. 25, 2005, 1 page.

PCT International Search Report and Written Opinion, PCT/US06/33098, Oct. 23, 2007, 11 pages.

* cited by examiner

B-B

DEVICE FOR BIOMETRICALLY CONTROLLING A FACE SURFACE

This application is the National Stage of International Application No. PCT/RU2005/000210, published in Russian under PCT Article 21(2), filed Apr. 20, 2005, which claims priority to International Application No. PCT/RU2004/000312, filed Aug. 12, 2004, both of which are incorporated by reference in their entirety.

FIELD OF ENGINEERING THE INVENTION RELATES TO

The invention relates to the devices for measuring surface contours and can be used for person identification in security systems.

STATE OF THE ART

A device for contactless control of the surface profile of objects is known, WO 00/70303 of Nov. 23, 2000, comprising of a pulse illumination unit provided with a pulse light source and a transparency, which forms a transparency image on an object surface, and an image recording unit.

The disadvantage of this device is that it is unpractical for biometrical control of a face profile, since it assumes arbitrary face orientation, which requires association of the face contour points with its image and complicates biometrical control of the face surface.

A device for biometrical control of a face surface is known, WO 02/09038 of Jan. 31, 2002, comprising a TV camera (image recording unit), a unit for displaying face position and a computer.

The disadvantage of this device is the low accuracy of measuring the position of the points on the face surface due to the fact that coordinates of these points are determined in plane only and not spatially, as well as the low operation rate of conducting a biometrical control, caused by the necessity of performing manual operations.

INVENTION DISCLOSURE

The invention aims at providing efficient biometric control of a face surface.

A technical result of utilization of this invention is an increase in control efficiency and accuracy in determining biometric face characteristics.

Described technical result is achieved by means of a device for biometrically controlling a face surface, which comprises a TV camera, a unit for displaying face position and a computer. This device additionally includes an illumination unit provided with a transparency and an objective lens for projecting transparency image on the face surface, which is arranged in such a way that optical axes of the objective lenses of the illumination unit and TV camera are disposed in one plane at an angle with respect to each other, while a unit for displaying face position is embodied and disposed in such a way that it makes it possible to display the symmetric face position with respect to the plane, formed by optical axes of the objective lenses of the illumination unit and TV camera.

The computer performs snap-association of the obtained contours of the face surface with the system of coordinates associated with a human face. For this purpose, the computer is provided with a capability to determine actual, asymmetrical face position with respect to the plane formed by the optical axes of the objective lenses of the illumination unit and a TV camera.

Objective lenses of the illumination unit and a TV camera can be positioned one under the other in such a way that their optical axes lie in a vertical plane and the unit for displaying a face position is positioned between them.

The transparency of the illumination unit can be realised in the form of a screen composed of parallel band segments and one band, which is transversal with respect to them along the axis of symmetry of the screen, and arranged in such a way that its transversal band is located in the vertical plane formed by the optical axes of the objective lenses of the illumination unit and TV camera.

The unit for displaying the face position can be realized in the form of a planar mirror with a band and arranged in such a way that the band is located in the plane formed by the optical axes of the objective lenses of the illumination unit and TV camera.

The unit for displaying the face position can be realized in the form of a two-face mirror or in the form of several two-face mirrors, edges of which are located in the plane formed by the optical axes of the objective lenses of the illumination unit and TV camera.

The unit for displaying the face position can be realized in the form of a TV screen with a vertical marking defining the location of the plane formed by the optical axes of the objective lenses of the illumination unit and TV camera.

BEST EMBODIMENT

Figure 1:
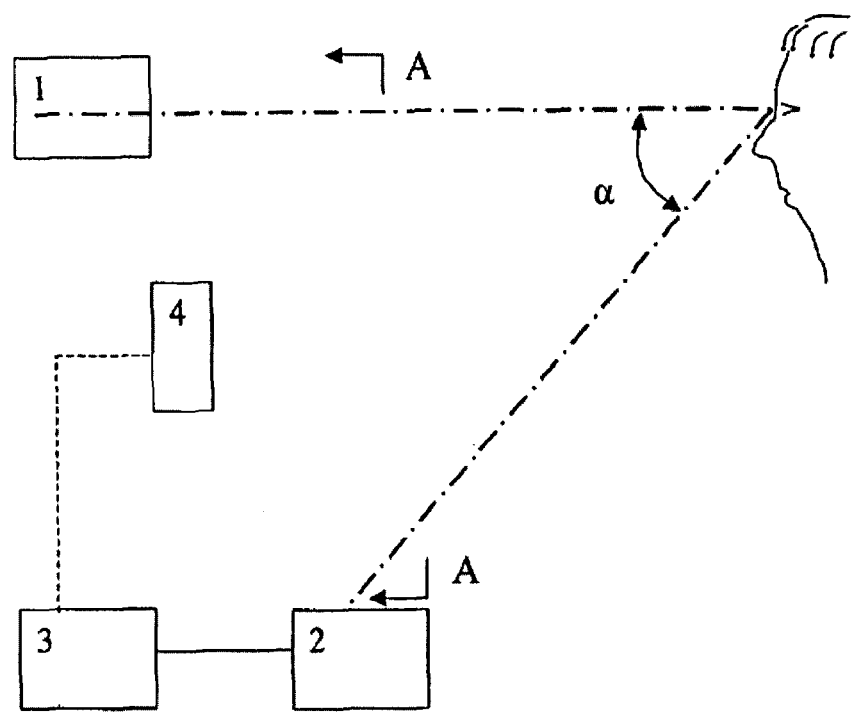
FIG. 1 shows the schematic of the device for biometrical control of a face surface.

According to the schematic shown in FIG. 1, the device includes an illumination block 1 provided with a transparency and an objective lenses for projecting the transparency image on the face surface, TV camera 2, computer 3 and a unit for displaying the face position 4.

Optical axes of the projecting objective lenses of the illumination unit 1 and TV camera 2 are disposed at an angle $\alpha$ with respect to each other.

The image of the transparency, distorted by the surface profile of the human face, is recorded by the TV camera and transmitted to the computer 3, which computes the height Z of the surface profile for a point with coordinates X,Y using the formula:

$$Z = \Delta Y / \tan(\alpha),$$

where $\Delta Y$ is a measure of the transparency image band distortion.

The computer determines characteristic points and fields of the face surface based on three coordinates.

Figure 2:
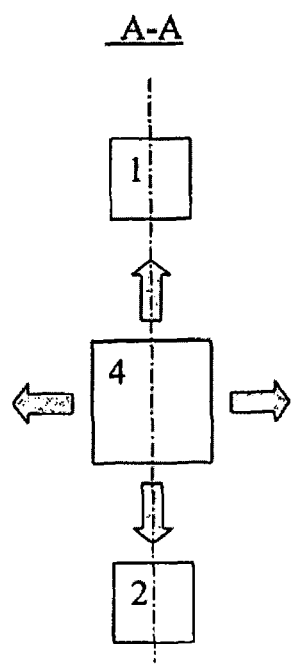
FIG. 2 schematically illustrates positioning of the device units as seen by a person at the time of biometrical control of his/her face.
Figure 3:
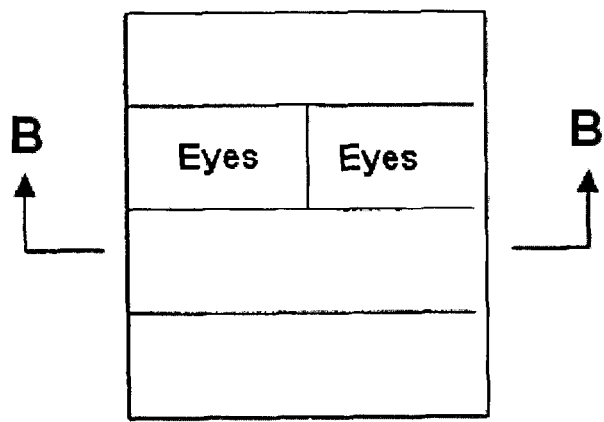
FIGS. 3, 4 and 5 schematically show a combined mirror unit for displaying a face position.
Figure 4:
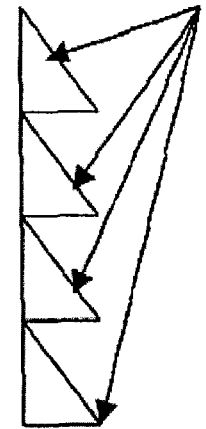
Figure 5:
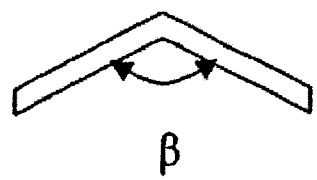

The person, whose face is being analysed, orients his/her face as shown in FIG. 2 using a unit for displaying the face position 4, which can be realized in the form of a mirror or a TV screen with vertical marking, which allows orienting a nose along the marking or eyes—symmetrically with respect to the marking. The display unit can be realized in the form of a two-face mirror or a series of two-face mirrors (see FIGS. 3, 4 and 5), whose edges are located in the plane formed by the optical axes of the objective lenses of the illumination unit and TV camera.

Realization of a transparency of the illumination unit 1 in the form of a line screen with transversal band located in the plane, formed by the optical axes of the objective lenses of the illumination unit and TV camera, allows a person to orient his/her face symmetrically with respect to this transversal band by observing it in the unit for displaying the face position. In this case, the nose is positioned along the band.

The illumination unit and TV camera can operate outside of the visible part of the optical range.

The computer is realized with a capability to determine the actual asymmetrical position of the face with respect to the plane formed by the optical axes of the objective lenses of the illumination unit and TV camera.

What is claimed is:

1. A device for biometrically controlling a face surface, the device comprising:
    an illumination unit with a transparency and an illumination-objective lens configured to project a transparency image on a face of a user such that the transparency image is distorted by the face of the user;
    a face-orientation unit configured to display a face position;
    a camera configured to capture a distorted image of the transparency image projected on and distorted by the face of the user, the camera including a camera-objective lens, the illumination-objective lens and the camera-objective lens each having an optical axis, the optical axis of the illumination-objective lens and the optical axis of the camera-objective lens being disposed in a common plane at an angle with respect to each other; and
    a computer communicatively coupled to the camera to receive the distorted image, the computer processing the distorted image to generate characteristic points and fields of the face based on three-dimensional coordinates for a surface profile of the face derived from the distorted image, the distorted image being a single distorted image,
    wherein the transparency of the illumination unit comprises a screen including a plurality of parallel band segments and one band transversal to the plurality of parallel band segments along an axis of symmetry of the screen, the one band transversal to the plurality of parallel band segments being located in a vertical plane formed by the optical axes of the objective lenses of the illumination unit and the camera.

2. The device according to claim 1, wherein the face-orientation unit for displaying the face position is located in between the illumination unit and the camera.

3. The device of claim 1, wherein processing includes measuring a transparency image band distortion.

4. A device for biometrically controlling a face surface, the device comprising:
    an illumination unit with a transparency and an illumination-objective lens configured to project a transparency image on a face of a user such that the transparency image is distorted by the face of the user;
    a face-orientation unit configured to display a face position;
    a camera configured to capture a distorted image of the transparency image projected on and distorted by the face of the user, the camera including a camera-objective lens, the illumination-objective lens and the camera-objective lens each having an optical axis, the optical axis of the illumination-objective lens and the optical axis of the camera-objective lens being disposed in a common plane at an angle with respect to each other; and
    a computer communicatively coupled to the camera to receive the distorted image, the computer processing the distorted image to generate characteristic points and fields of the face based on three-dimensional coordinates for a surface profile of the face derived from the distorted image, the distorted image being a single distorted image,
    wherein the face-orientation unit includes one or more two-face mirrors having edges located in the common plane formed by the optical axes of the objective lenses of the illumination unit and the camera.

5. The device according to claim 4, wherein the face-orientation unit is located between the illumination unit and the camera.

6. A device for biometrically controlling a face surface, the device comprising:
    an illumination unit with a transparency and an illumination-objective lens configured to project a transparency image on a face of a user such that the transparency image is distorted by the face of the user;
    a face-orientation unit configured to display a face position;
    a camera configured to capture a distorted image of the transparency image projected on and distorted by the face of the user, the camera including a camera-objective lens, the illumination-objective lens and the camera-objective lens each having an optical axis, the optical axis of the illumination-objective lens and the optical axis of the camera-objective lens being disposed in a common plane at an angle with respect to each other; and
    a computer communicatively coupled to the camera to receive the distorted image, the computer processing the distorted image to generate characteristic points and fields of the face based on three-dimensional coordinates for a surface profile of the face derived from the distorted image, the distorted image being a single distorted image,
    wherein the face-orientation unit includes a screen with a vertical marking defining the position of the common plane formed by the optical axes of the objective lenses of the illumination unit and the camera.

7. The device according to claim 6, wherein the face-orientation unit is located between the illumination unit and the camera.

8. A device according to claim 1 for biometrically controlling a face surface, the device comprising:
    an illumination unit with a transparency and an illumination-objective lens configured to project a transparency image on a face of a user such that the transparency image is distorted by the face of the user;
    a face-orientation unit configured to display a face position;
    a camera configured to capture a distorted image of the transparency image projected on and distorted by the face of the user, the camera including a camera-objective lens, the illumination-objective lens and the camera-objective lens each having an optical axis, the optical axis of the illumination-objective lens and the optical axis of the camera-objective lens being disposed in a common plane at an angle with respect to each other; and
    a computer communicatively coupled to the camera to receive the distorted image, the computer processing the distorted image to generate characteristic points and fields of the face based on three-dimensional coordinates for a surface profile of the face derived from the distorted image, the distorted image being a single distorted image, wherein the face-orientation unit is adapted to display a symmetrical face position with respect to the common plane formed by the optical axes of the objective lenses of the illumination unit and the camera.

9. The device according to claim 8, wherein the face-orientation unit is located between the illumination unit and the camera.

10. A method for biometrically controlling a face surface, the method comprising:
projecting, with an illumination unit, a transparency image on a face of a user such that the face of the user distorts the transparency image;
receiving, with a camera, a single distorted image of the transparency image projected on and distorted by the face of the user, the illumination unit and the camera each having an objective lens with an optical axis, the optical axes of the illumination unit and the camera being disposed in a common plane at an angle with respect to each other;
transmitting the distorted image to a computer; and
processing, with the computer, the distorted image to generate characteristic points and fields of the face based on three-dimensional coordinates for a surface profile of the face derived from the single distorted image,
wherein a transparency of the illumination unit comprises a screen including a plurality of parallel band segments and one band transversal to the plurality of parallel band segments along an axis of symmetry of the screen, the one band transversal to the plurality of parallel band segments being located in a vertical plane formed by the optical axes of the objective lenses of the illumination unit and the camera.

11. The method according to claim 10, wherein a face-orientation unit for displaying a face position is located in between the illumination unit and the camera.

12. The method according to claim 10, wherein a face-orientation unit for displaying a face position includes one or more two-face mirrors having edges located in the common plane formed by the optical axes of the objective lenses of the illumination unit and the camera.

13. The method according to claim 10, wherein a face-orientation unit for displaying a face position includes a screen with a vertical marking defining the position of the common plane formed by the optical axes of the objective lenses of the illumination unit and the camera.

14. The method according to claim 10, wherein a face-orientation unit for displaying the face position is adapted to display a symmetrical face position with respect to the common plane formed by the optical axes of the objective lenses of the illumination unit and the camera.

15. The method of claim 10, wherein processing includes measuring a transparency image band distortion.

16. A method for biometrically controlling a face surface, the method comprising:
projecting, with an illumination unit, a transparency image on a face of a user such that the face of the user distorts the transparency image;
receiving, with a camera, a single distorted image of the transparency image projected on and distorted by the face of the user, the illumination unit and the camera each having an objective lens with an optical axis, the optical axes of the illumination unit and the camera being disposed in a common plane at an angle with respect to each other;
transmitting the distorted image to a computer; and
processing, with the computer, the distorted image to generate characteristic points and fields of the face based on three-dimensional coordinates for a surface profile of the face derived from the single distorted image,
wherein processing includes measuring a transparency image band distortion, and
wherein one of the three-dimensional coordinates is determined based on $Z=\Delta Y/\tan(\alpha)$, where $Z$ is the height of the surface profile, $\Delta Y$ is the measure of the transparency image band distortion, and $\alpha$ is the angle.

17. The method according to claim 16, further comprising displaying, with a face-orientation unit, a face position, the face-orientation unit being located between the illumination unit and the camera.

18. The method according to claim 16, further comprising displaying, with a face-orientation unit, a face position, the face-orientation unit including one or more two-face mirrors having edges located in the common plane formed by the optical axes of the objective lenses of the illumination unit and the camera.

19. The method according to claim 16, further comprising displaying, with a face-orientation unit, a face position, the face-orientation unit includes a screen with a vertical marking defining the position of the common plane formed by the optical axes of the objective lenses of the illumination unit and the camera.

20. A device for biometrically controlling a face surface, the device comprising:
an illumination unit with a transparency and an illumination-objective lens configured to project a transparency image on a face of a user such that the transparency image is distorted by the face of the user;
a face-orientation unit configured to display a face position;
a camera configured to capture a distorted image of the transparency image projected on and distorted by the face of the user, the camera including a camera-objective lens, the illumination-objective lens and the camera-objective lens each having an optical axis, the optical axis of the illumination-objective lens and the optical axis of the camera-objective lens being disposed in a common plane at an angle with respect to each other; and
a computer communicatively coupled to the camera to receive the distorted image, the computer processing the distorted image to generate characteristic points and fields of the face based on three-dimensional coordinates for a surface profile of the face derived from the distorted image, the distorted image being a single distorted image,
wherein processing includes measuring a transparency image band distortion, and
wherein one of the three-dimensional coordinates is determined based on $Z=\Delta Y/\tan(\alpha)$, where $Z$ is the height of the surface profile, $\Delta Y$ is the measure of the transparency image band distortion, and $\alpha$ is the angle.

* * * * *